United States Patent [19]
Jaraczewski et al.

[11] Patent Number: 5,938,694
[45] Date of Patent: Aug. 17, 1999

[54] ELECTRODE ARRAY CATHETER

[75] Inventors: Richard S. Jaraczewski, Livermore; Kevin C. Ladd, Redwood City; Mark A. Maguire, San Jose; Ramiro L. Reyes, Pleasanton, all of Calif.

[73] Assignee: Medtronic CardioRhythm, San Jose, Calif.

[21] Appl. No.: 08/603,561

[22] Filed: Feb. 21, 1996

Related U.S. Application Data

[63] Continuation of application No. 08/150,624, Nov. 10, 1993, abandoned.

[51] Int. Cl.$^6$ ................................................. A61B 5/0402
[52] U.S. Cl. ........................................ 607/122; 600/373
[58] Field of Search ........................... 128/642; 607/122, 607/125, 126, 127, 119, 101, 102, 116, 118, 148; 600/373

[56] References Cited

U.S. PATENT DOCUMENTS

| | | |
|---|---|---|
| 4,522,212 | 6/1985 | Gelinas et al. . |
| 4,565,200 | 1/1986 | Cosman .................................. 128/736 |
| 4,649,924 | 3/1987 | Taccardi . |
| 4,660,571 | 4/1987 | Hess et al. . |
| 4,699,147 | 10/1987 | Chilson et al. . |
| 4,777,955 | 10/1988 | Brayton . |
| 4,860,769 | 8/1989 | Fogarty et al. . |
| 4,920,980 | 5/1990 | Jackowski ............................... 128/642 |
| 4,940,064 | 7/1990 | Desai . |
| 5,005,587 | 4/1991 | Scott . |
| 5,016,808 | 5/1991 | Heil, Jr. et al. . |
| 5,052,407 | 10/1991 | Hauser et al. .......................... 607/125 |
| 5,123,422 | 6/1992 | Charvin . |
| 5,156,151 | 10/1992 | Imran . |
| 5,181,511 | 1/1993 | Nickolls . |
| 5,237,996 | 8/1993 | Waldman et al. ....................... 128/642 |
| 5,238,005 | 8/1993 | Imran . |
| 5,275,162 | 1/1994 | Edwards et al. ........................ 128/642 |

(List continued on next page.)

FOREIGN PATENT DOCUMENTS

| | | |
|---|---|---|
| A-0479435 | 4/1982 | European Pat. Off. . |
| A-0073881 | 3/1983 | European Pat. Off. . |
| A-0280564 | 8/1988 | European Pat. Off. . |
| A-0479435 | 4/1992 | European Pat. Off. . |
| A-0499491 | 8/1992 | European Pat. Off. . |
| A-0563614 | 10/1993 | European Pat. Off. . |
| WO-A-8304182 | 12/1983 | WIPO . |
| WO-A-9220401 | 11/1992 | WIPO . |
| WO-A-9300958 | 1/1993 | WIPO . |
| WO-A-9315790 | 8/1993 | WIPO . |
| WO-A-9316755 | 9/1993 | WIPO . |
| WO-A-9321990 | 11/1993 | WIPO . |
| PCT/US94/11756 | 10/1994 | WIPO . |

*Primary Examiner*—Brian L. Casler
*Attorney, Agent, or Firm*—Townsend and Townsend and Crew LLP

[57] ABSTRACT

An electrode array catheter, typically used for mapping, pacing and ablation, includes a flexible delivery sheath (36, 64) and an electrode assembly (2, 62) slidably mounted within the delivery sheath for movement between retracted and deployed positions. The electrode assembly includes an ablation electrode (10, 90) and a plurality of mapping electrodes (26, 114) which are grouped in pairs and naturally assume a three-dimensional array when deployed. The electrodes are distributed to contact a portion of the chamber wall (130) surrounding the target site. The electrode assembly tip has a coiled conical shape (24) in one embodiment and has a number of axially extending, radially outwardly curved arms (118) in another embodiment. A flat flexible circuit (110), having axially extending electrode traces (112) connecting proximal terminals (108) to distal electrode pads (114), is slit (116) axially and is preformed and to create the curved arms.

37 Claims, 6 Drawing Sheets

U.S. PATENT DOCUMENTS

| | | | |
|---|---|---|---|
| 5,279,299 | 1/1994 | Imran . | |
| 5,282,845 | 2/1994 | Bush et al. | 607/127 |
| 5,318,525 | 6/1994 | West et al. | 607/122 |
| 5,327,889 | 7/1994 | Imran | 607/122 |
| 5,327,905 | 7/1994 | Avitall . | |
| 5,365,926 | 11/1994 | Desai | 607/122 |
| 5,500,012 | 3/1996 | Brucker et al. . | |
| 5,626,136 | 5/1997 | Webster, Jr. . | |

ELECTRODE ARRAY CATHETER

This is a Continuation of application Ser. No. 08/150,624, filed Nov. 10, 1993, now abandoned.

BACKGROUND OF THE INVENTION

The present invention relates generally to steerable catheters, and more specifically to steerable electrophysiology catheters for use in mapping and ablation of the heart.

The heart includes a number of pathways which are responsible for the propagation of signals necessary for normal electrical and mechanical function. The present invention is concerned with treatment of tachycardia, abnormally rapid rhythms of the heart caused by the presence of an arrhythmogenic site or accessory pathway which bypasses or short circuits the normal pathways in the heart. Tachycardias may be defined as ventricular tachycardias (VTs) and supraventricular tachycardias (SVTs). VTs originate in the left or right ventricle and are typically caused by arrhythmogenic sites associated with a prior myocardial infarction. SVTs originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, drugs typically only mask the symptoms and do not cure the underlying cause. Implantable devices, on the other hand, usually can correct an arrhythmia only after it occurs. Surgical and catheter-based treatments, in contrast, will actually cure the problem usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention, are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue to ablate a region of the tissue which forms part of the arrhythmogenic site or the accessory pathway. By successfully destroying that tissue, the abnormal signaling patterns responsible for the tachycardia cannot be sustained. Methods and systems for performing RF ablation by controlling temperature at the ablation site are described in co-pending application Ser. No. 07/866,683 entitled "Method and System for Radiofrequency Ablation of Cardiac Tissue," filed Apr. 10, 1992, the complete disclosure of which is hereby incorporated by reference.

Catheters designed for mapping and ablation frequently include a number of individual electrode bands mounted to the distal tip of the catheter so as to facilitate mapping of a wider area in less time, or to improve access to target sites for ablation. Such catheters are described in co-pending application Ser. No. 07/866,383, filed Apr. 10, 1992, the complete disclosure of which is incorporated herein by reference. As described in that application, it is frequently desirable to deflect the distal tip of the catheter into a non-linear configuration such as a semicircle, which facilitates access to substantially all of the heart walls to be mapped or ablated. Such deflection may be accomplished through the use of pull wires secured to the distal tip which can be tensioned from the proximal end of the catheter to deflect the tip in the desired configuration. In addition, mapping and ablation catheters may facilitate rotational positioning of the distal tip, either by rotating the entire catheter from the proximal end, or, in the catheter described in co-pending application Ser. No. 07/866,383, the disclosure of which is incorporated by reference, by exerting torque on a core wire secured to the distal tip without rotating the catheter body itself.

Catheters utilized in radiofrequency ablation are inserted into a major vein or artery, usually in the neck or groin area, and guided into the chambers of the heart by appropriate manipulation through the vein or artery. Such catheters must facilitate manipulation of the distal tip so that the distal electrode can be positioned against the tissue region to be ablated. The catheter must have a great deal of flexibility to follow the pathway of the major blood vessels into the heart, and the catheter must permit user manipulation of the tip even when the catheter is in a curved and twisted configuration. Because of the high degree of precision required for proper positioning of the tip electrode, the catheter must allow manipulation with a high degree of sensitivity and controllability. In addition, the distal portion of the catheter must be sufficiently resilient in order to be positioned against the wall of the heart and maintained in a position during ablation without being displaced by the movement of the beating heart. Along with steerability, flexibility, and resiliency, the catheter must have a sufficient degree of torsional stiffness to permit user manipulation from the proximal end.

One of the problems with current technology relates to quickly mapping a large surface area of the heart. Finding the target site using conventional catheters with linear electrode orientations is a tedious activity requiring multiple catheter placements. Balloon or basket type mapping catheters, providing three dimensional arrays of endocardial mapping electrodes, have been developed. However, these arrangements are typically designed to engage virtually the entire chamber wall, as opposed to a part or region of the chamber wall. Such full-chamber type mapping catheters lack the ability to direct an ablation electrode to a target site, so they are used for mapping only. Also, by virtue of their design, which is intended to cover virtually the entire chamber wall, these full-chamber type mapping catheters will necessarily lack the ability to concentrate the mapping electrodes at the region of the target site. Thus, while information may be obtainable from the entire chamber wall, much of it may not be useful since it is not near the target site. Also, because these devices fill an entire heart chamber, they may partially occlude blood flow or cause coagulation of blood, that is, create blood clots.

SUMMARY OF THE INVENTION

Electrode array catheters according to the present invention are useful for a variety of electrophysiology procedures, including mapping, pacing and ablation therapy. The catheter includes a flexible delivery sheath having an hollow interior and proximal and distal ends. The invention addresses and solves the problem of mapping a portion of the chamber wall of the heart in the vicinity of a target site in a relatively short time span.

An electrode assembly is slidably mounted within the hollow interior of a delivery sheath for movement between retracted and deployed positions. The electrode assembly includes a plurality of electrodes which naturally assume a two or a three dimensional array when they are at the deployed position. The electrodes are distributed to be able to contact and conform to the portion of the chamber wall at the target site when in the deployed position. One or more of the electrodes, which may include a central electrode, are preferably higher power, ablation electrodes. The ablation electrodes may be physically larger than the other electrodes, typically electrodes used for mapping or pacing, to accommodate higher energy flows.

The electrode assembly assumes a coiled conical shape when in the deployed position in one embodiment. Electrodes are preferably at spaced apart positions along the coiled, conically shaped electrode body to create a series of electrode pairs. In another embodiment, the electrode assembly includes a number of axially extending, radially outwardly curved arms. The mapping electrodes are also preferably positioned as electrode pairs along the curved arms.

The curved arms of the electrode assembly are preferably formed by a flat conductor cable having a plurality of axially extending electrode traces connecting proximal terminals to distal, exposed electrode pads; the electrode pads act as the mapping electrodes. The flat conductor cable is slit axially along at least part of its length and then formed into a tube-like member to create the curved arms.

The mapping electrodes are not typically suitable for ablation due to the size limitations of the conductor wires and the size of the electrodes. However, the current carrying capacity of the wires, signal traces and electrode pads could be increased, such as by increasing their size, a change of material, by cooling the various components, etc. Also, techniques may be developed which allow the delivery of energy sufficient to ablate tissue along what is now considered low energy wires, traces and electrodes. With the present invention, ablation may be successful with lower power/smaller lesions since the electrode array can be more accurately located near the target site; this accuracy of placement may permit local "mapping/pacing" electrode pairs to be used for RF energy delivery and ablation.

One of the advantages of the invention is that, by producing a three-dimensional area array of electrodes designed to engage only a portion of the chamber wall of the heart, a relatively large, but much less than the entire, surface area of the heart can be mapped precisely and in a relatively short time span. Since the physician generally knows the approximate area where the target site is located on the chamber wall surface, mapping of the entire chamber wall is not generally needed. Therefore, a more localized concentration of electrodes can be used with the present invention than would be typical of a chamber-filling device. This helps the device made according to the present invention be simpler to use and the resulting information easier to process. Conventional chamber-filling mapping probes also may not be suitable for ablation, only mapping.

The pinpointing of a target site for ablation can be speeded up dramatically without the multiple catheter placements necessary with conventional linear electrodes. The invention also permits the application of a greater number of electrodes against the portion of the chamber wall being investigated than is possible with conventional large diameter linear electrode catheters.

Another advantage of the invention over the prior art is the ability of the electrodes to conform to the region of the chamber wall being mapped. Electrodes, which preferably are in closely spaced pairs, provide the user with specific information regarding the electrical activity within the region regardless of the surface contour.

Other features and advantages of the invention will appear from the following description in which the preferred embodiments have been set forth in detail in conjunction with the accompanying drawings.

DESCRIPTION OF THE PREFERRED EMBODIMENTS

The invention is directed to an electrode array catheter such as shown in FIGS. 1–7. An exemplary catheter constructed in accordance with the principles of the present invention includes an electrode assembly 2 which will be described with reference to FIGS. 1–4 and a steerable delivery catheter 4 shown in FIGS. 5–7. All dimensions given for each embodiment are exemplary only, and it will be appreciated that specific dimensions may be varied considerably while remaining within the scope of the present invention.

Figures 1, 2, 2A, 2B, 2C, 3A, 3B, 3C:
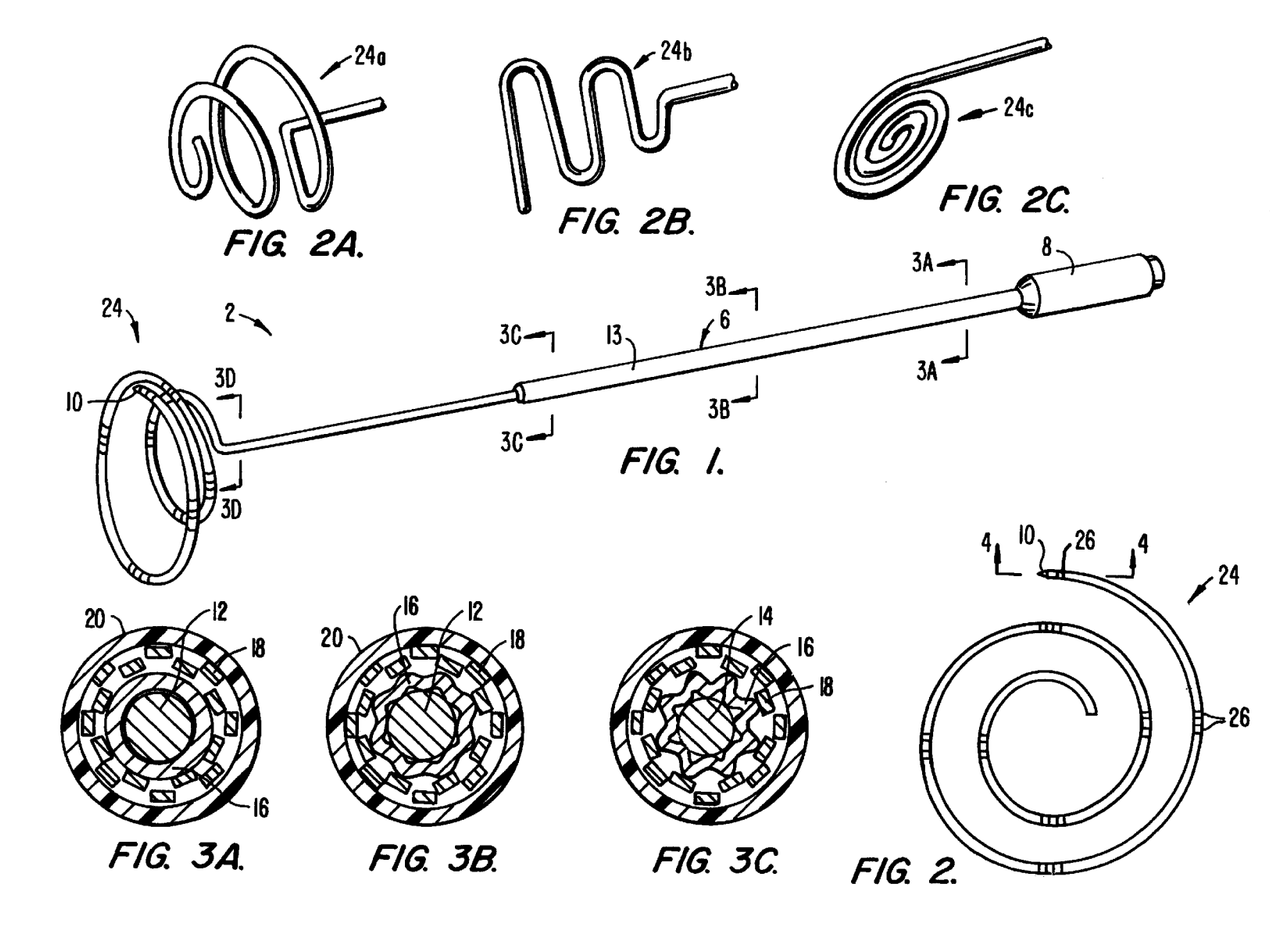
FIG. 1 is a simplified perspective view of an electrode assembly of a first embodiment of the invention having the coiled, conical tip.
FIG. 2 is an enlarged end view of the coiled, conical tip of FIG. 1.
FIGS. 2A–2C illustrate electrode assembly tips having an inverted conical shape, a planar serpentine shape and a planar coil shape, respectively.
FIGS. 3A–3D are cross-sectional views of the electrode assembly taken along lines 3A—3A through 3D—3D in FIG. 1 respectively.

Electrode assembly 2 includes an electrode catheter body 6 extending from an electrical connector 8 at a proximal end to a tip electrode 10 at a distal end. Body 6, as shown in FIGS. 3A and 3B, includes a 0.46 mm (0.018 inch) diameter stainless steel support mandrel 12 extending from connector 8 to a transition region 13 and a 0.31 mm (0.015 inch) core 14 extending from core transition region 13 to tip electrode 10. A 0.71 mm (0.028 inch) OD/0.51 mm (0.020 inch) ID stainless steel hypotube 16 surrounds support mandrel 12 and an initial portion of core 14. See FIGS. 3A–3C. Hypotube 16 extends a relatively short distance past core transition region 13 and is crimped, as shown in FIGS. 3B and 3C, onto the abutting ends of support mandrel 12 and core 14 at transition region 13. A number, sixteen in the preferred embodiment, of insulated conductor wires 18 are located about hypotube 16 within an outer Pebax jacket 20 having a 1.12 mm (0.044 inch) ID and a 1.32 mm (0.052 inch) OD. Pebax is the trademark for a polyether block polyamide copolymer made by Elf Atochem, Inc. of Philadelphia, Pa. Just past transition region 13, a smaller Pebax jacket 22 having a 0.79 mm (0.031 inch) ID and a 0.94 mm (0.037 inch) OD is used. Core 14 is preferably made from a super elastic spring material, such as nickel-titanium alloys (NiTi), such as that available from Furukawa Electric Company Ltd. of Tokyo, Japan. NiTi is preferred for core 14 because it is very resilient and has a very good spring memory for its prior shape, even when highly flexed. Other highly deformable spring materials, such as spring steel or braided/coiled spring materials, might also be used.

In the embodiment of FIGS. 1–4, the tip 24 of the catheter is made so that it assumes a coiled conical shape as shown in FIGS. 1 and 2. Electrode assembly 2, when inserted into delivery catheter 4, will have its tip 24 in a straightened orientation since it is, prior to deployment, housed within delivery catheter 4. Only after tip 24 is moved to its deployed position external of delivery catheter 4 will the tip assume its coiled conical shape. Tip 24 can also be made as an inverted coil tip 24a, a planar serpentine tip 24b or a flat coil tip 24c as illustrated in FIGS. 2A–2C.

Tip 24 includes fifteen electrodes 26 along its length. Fourteen of electrodes 26 are spaced apart by about 0.5–2.0 mm, typically about 1 mm, to form 7 pairs of electrodes. Distal electrode 27 is paired with tip electrode 10, as shown in more detail in FIG. 4 for mapping. NiTi core 14 is seen to be surrounded by a polyimide sleeve 28 having a 0.45 mm (0.0179 inch) OD and a 0.40 mm (0.0159 inch) ID. Sleeve 28 provides electrical insulation between core 14 and the electrodes 26/conductor wires 18. Conductor wires 18 are electrically connected to electrodes 26 and tip electrode 10 in the manner indicated in FIG. 4. Tip electrode 10 and the conductor wire 18 connected to the tip electrode are sufficiently heavy duty to permit electrode 10 to be used as an ablation electrode using RF electrical energy. Tip electrode 10 can also be used for mapping in conjunction with electrode 27 positioned adjacent the tip electrode.

Figures 3D, 4, 5:
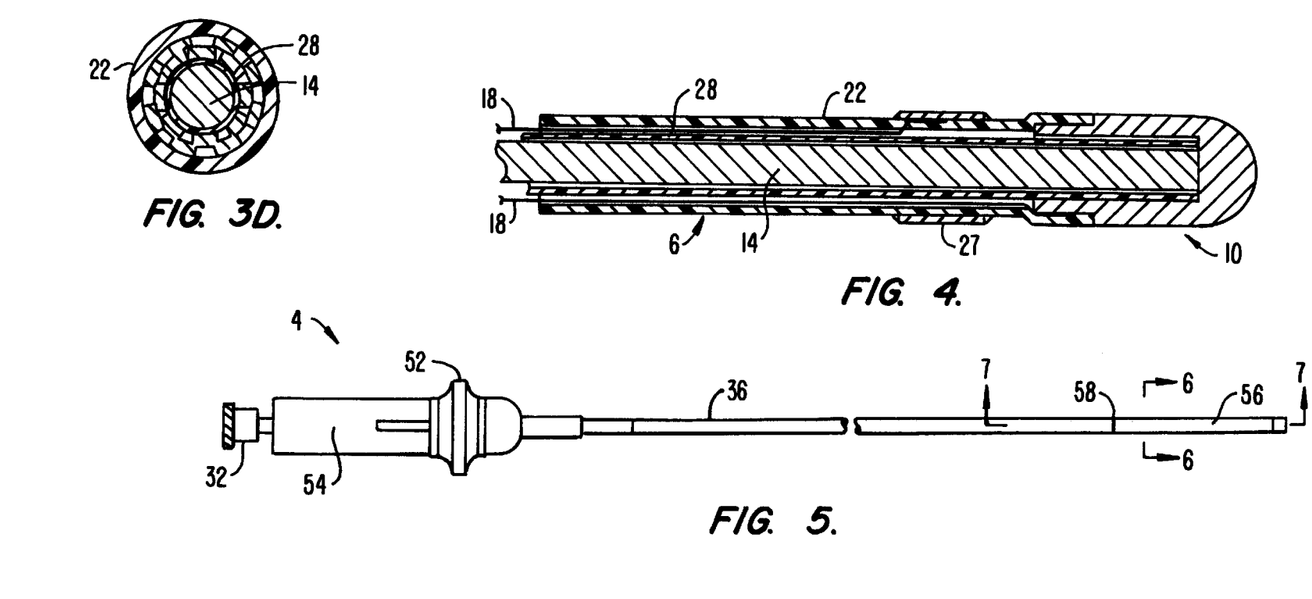
FIG. 4 is an enlarged cross-sectional view taken along line 4—4 of FIG. 2.
FIG. 5 is a simplified side view of a steerable delivery catheter used with the electrode assembly of FIG. 1 to create a first embodiment of an electrode array catheter made according to the invention.

It may be desired to use electrodes other than tip electrode 10 for ablation. This may be accommodated by increasing the axial length of selected electrodes 26 from about 0.5 mm to 1.0 mm to about 1 to 10 mm. To maintain the desired flexibility of tip 24, the extended length ablation-capable electrodes 26 can be made, for example, as a spiral coil about sleeve 28 instead of a band as illustrated in FIG. 4. Also, ablation-capable electrodes 26 could be made of braided material.

Figure 6:
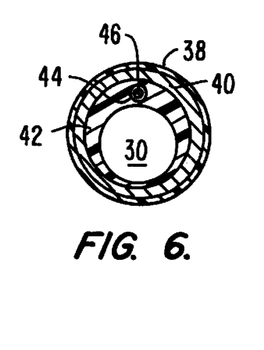
FIGS. 6 and 7 are cross-sectional views taken along lines 6—6 and 7—7 of FIG. 5, respectively.
Figure 7:
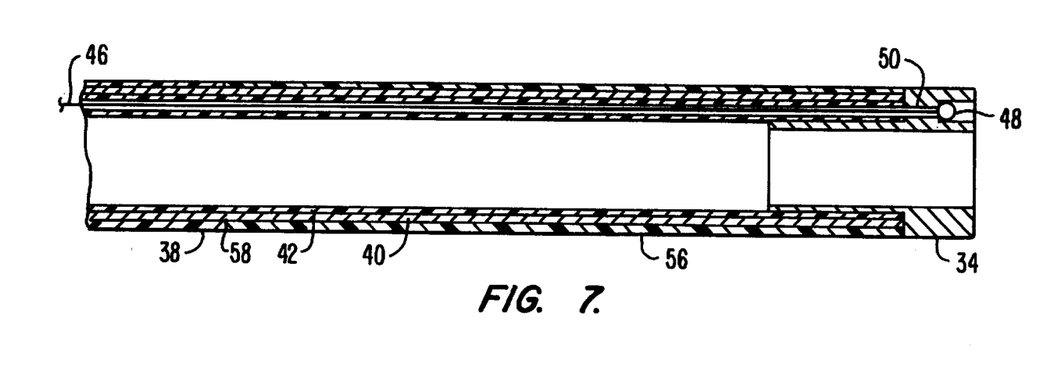

Steerable delivery catheter 4, see FIGS. 5–7, is designed for use with electrode assembly 2. Catheter 4 has a hollow interior 30 extending along its entire length from Luer lock fitting 32 at its proximal end to a tip ring 34 at its distal end. Catheter 4 includes a catheter body 36 having a Pebax jacket 38 surrounding a braided layer 40. A TFE liner 42 is within braided layer 40 and provides a lubricious surface for the passage of electrode assembly 2 within hollow interior 30 formed within liner 42. Other lubricious materials, such as FEP, ETFE or PE, could be used instead of TFE for liner 42.

Hollow interior 30 is formed eccentrically within TFE liner 42 to provide room for an axial bore 44 housing a TFE-coated manipulator wire 46. Manipulator wire 46 has a ball 48 at its distal end which is too large to fit through a bore 50 in tip ring 34. The proximal end, not shown, of manipulator wire is connected to a tip deflection control 52 mounted to a handle 54.

The distal end of catheter body 36 includes a deflecting section 56 distal of a jacket transition line 58. Deflecting section 56 is less stiff than the proximal end of catheter body to allow deflecting section 56 to be sufficiently flexible for the proper guidance by wire 46 while providing appropriate structural integrity for the remainder of catheter body 36. Tip deflection control 52 is preferably an axially movable type so that pulling on control 52 causes the distal end of catheter body 36 to deflect. Other types of controls could be used as well. Also, more than one manipulator wire 46 could be used.

In use, electrode assembly 2 has its tip 24 preformed into the coiled, conical shape of FIG. 1. Electrode tip 24 is then inserted through Luer lock fitting 32 and into hollow interior 30. Electrode assembly 2 is continued to be directed through hollow interior 30 until tip electrode 10 is just proximal to deflecting section 56. Using appropriate surgical techniques, the catheter is guided into the heart chamber under consideration. Near the target site to be investigated or treated, electrode assembly 2 is pushed axially and distally until tip 24 extends past tip ring 34 and assumes a coiled, conical shape. Tip 24 can then be placed against the chamber wall at the target site under consideration. If desired, tip 24 may be manipulated to deflect laterally and torque around the longitudinal axis of body 6 prior to being placed against the chamber wall. The flexibility and resilience of tip 24 is such that it will closely conform to the shape of the chamber wall at the target site, whether it be flat, convex, concave, or a combination. This conformance ensures a maximum number of electrodes 26 will actually contact the chamber wall.

A separate conductor could be used on steerable delivery catheter 6 to deliver RF energy for ablation to an electrode mounted as the tip ring 34. It may be possible to do this through the use of manipulator wire 46 as both the manipulator wire and as an electrical conductor.

Figures 8, 8A:
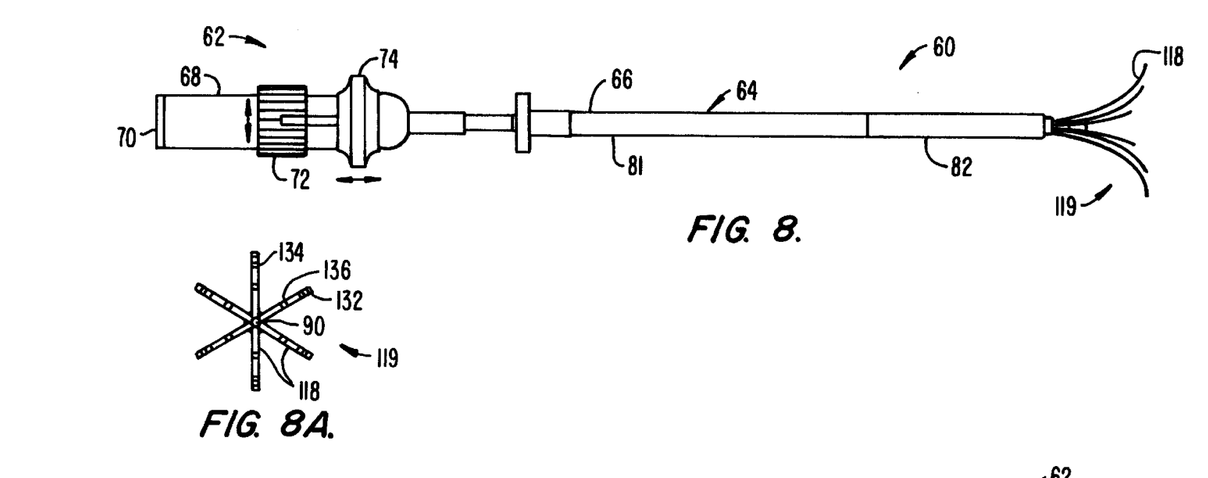
FIG. 8 is a simplified side view of an alternative embodiment of an electrode array catheter made according to the invention.
FIG. 8A is an end view of the electrode array of FIG. 8.
Figure 9:
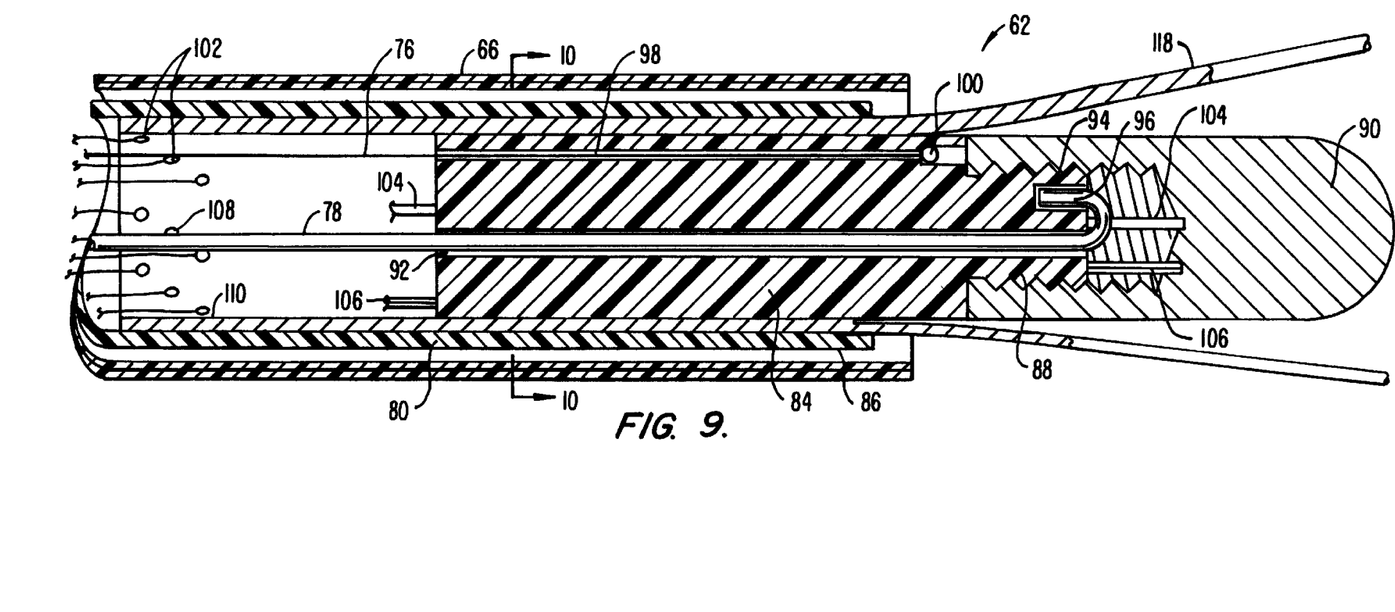
FIG. 9 is an enlarged cross-sectional view of a portion of the tip of the catheter of FIG. 8.
Figure 10:
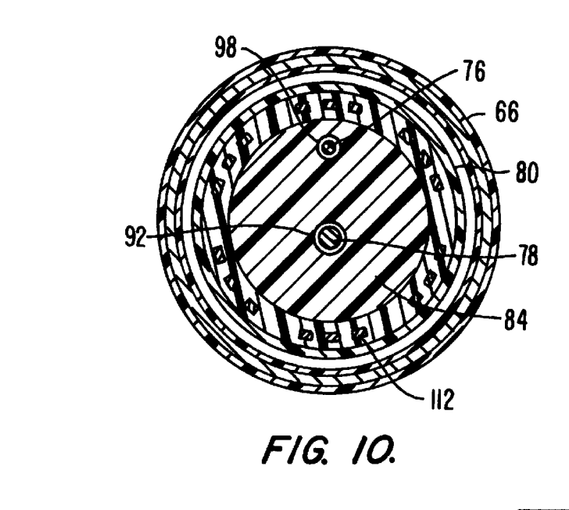
FIG. 10 is a cross-sectional view taken along line 10—10 of FIG. 9.

FIGS. 8–10 illustrate a second embodiment of the invention. Electrode array catheter 60 includes a steerable electrode catheter 62 and a tubular delivery sheath 64. Catheter 62 passes through and is slidably mounted within tubular delivery sheath 64. Catheter 62 includes a handle 68 having an electrical connector 70 at a proximal end, a twist-type, lateral deflection knob 72 and an axially moveable tip deflection control 74. Tip deflection control 74 is connected to a manipulator wire 76 of electrode catheter 62; see FIGS. 9 and 10. Lateral deflection knob 72 is connected to and is used to rotate a core wire 78 of catheter 62. Handle 68 can be of a conventional design or can be made as shown in U.S. patent application Ser. No. 08/095,447 filed Jul. 20, 1993 entitled, "Multicurve Deflectable Catheter," the disclosure of which is incorporated by reference.

Delivery sheath 64 is preferably a three layer sheath having an outer Pebax layer, a stainless steel braided layer and a TFE liner. Delivery sheath 64 changes its flexibility over its length and includes a proximal, stiffer portion 81 and distal, softer and more flexible portion 82. The outer surface of proximal portion 81 preferably has a Durometer reading of about 50 to 80, and more preferably about 70 while the distal portion 82 preferably has a Durometer reading of about 30 to 50, and more preferably about 35.

Electrode catheter 62 includes an insulator body 84, preferably made of PEEK (poly-ether-ether-ketone), housed within the distal end 86 of Pebax jacket 80. Insulator body 84 has a threaded tip 88 to which a metal tip electrode 90 is mounted; other mounting structures, such as a snap-fit fitting, could be used instead of threads. Body 84 also includes a central bore 92 through which core wire 78 passes. Threaded tip 88 of body 84 has a shallow recess 94 within which the distal end 96 of core 78 is housed. Core wire 78 is secured to insulator body 84, typically using an adhesive. This provides axial integrity between the ends of catheter assembly 60. Rotating core wire 78 causes transmission of torque to, and causes the rotation of, electrode catheter 62.

Body 84 has an additional, radially offset bore 98 through which manipulator wire 76 passes. Manipulator wire 76 has an enlarged tip 100 which prevents manipulator wire 76 from being pulled back through offset bore 98. This permits the user to deflect the tip of delivery sheath 64 when guiding catheter 60 into position.

Electrode catheter 62 includes a set of mapping electrode wires 102, a power electrode wire 104 and a pair of thermocouple wires 106. Power electrode wire 104 and thermocouple wires 106 pass through bores, not shown, in insulator body 84 and are connected to tip electrode 90. Power electrode wire 104 is sufficiently heavy duty to permit tip electrode 90 to be used for both ablation using RF electrical energy and for mapping.

Figures 12, 14:
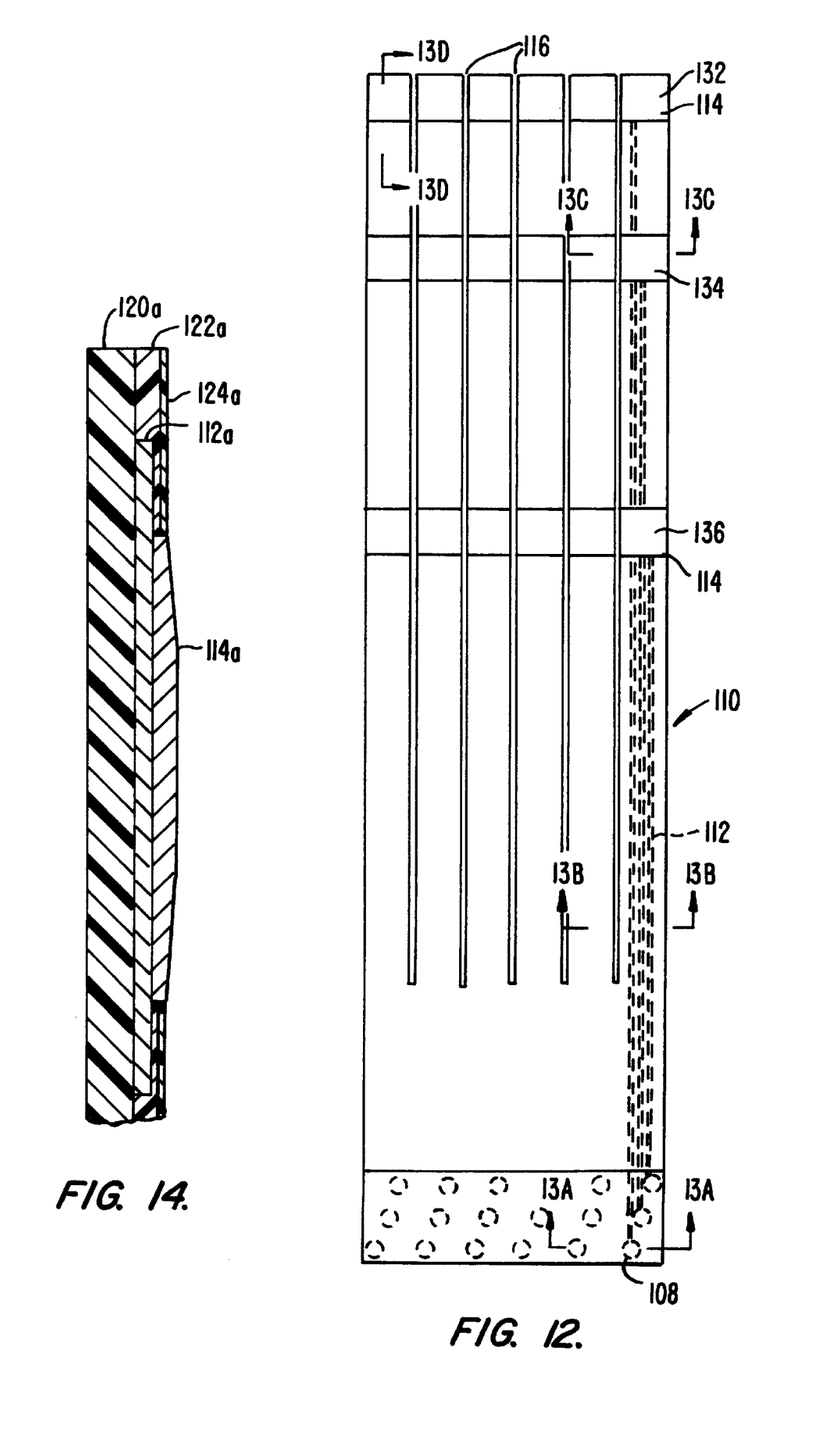
FIG. 12 is a plan view of a flat conductor cable for use with the electrode assembly of FIG. 9 with the proximal terminals with electrode traces shown in dashed lines for one of the electrode arms.
FIG. 14 illustrates an alternative embodiment of the structure shown in FIG. 13C.

The distal ends of wires 102 are soldered (or otherwise secured to provide electrical conductivity) to proximal terminals 108 formed on a flat flexible circuit 110. Flat flexible circuit 110 is shown in FIG. 12 in its flat configuration prior to being formed into the flared tubular shape of FIGS. 8 and 9. With reference to FIGS. 12–13E, flat flexible circuit 110 is shown to include a number of electrical traces 112 connecting exposed proximal terminals 108 to exposed electrode pads 114. Flexible circuit 110 has five slits 116 extending along substantially the entire length of the circuit so to create six electrode elements 118. Electrode elements 118 form a number of axially extending, radially outwardly curved arms having electrode pads 114 disposed on their inner surfaces so to contact a chamber wall during use. The electrode arms are preferably 1 mm wide, but could be from 0.1 mm to 2 mm wide, depending on the number of electrodes and traces. The electrode elements (arms) could be made as individual flex circuits rather than a slitted, single circuit. Electrode arms 118 with electrode pads 114 and electrode 90 form a petal-like array 119 at the distal end of electrode catheter 62. Array 119 has a deployed diameter of about 25 mm; the deployed diameter preferably ranges from about 10 mm to about 100 mm.

Figure 13A:
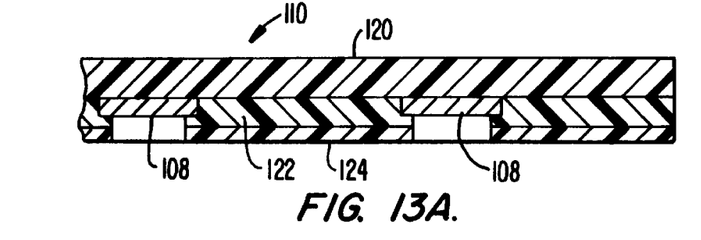
FIGS. 13A–13D are cross-sectional views taken along lines 13A—13A through 13D—13D of FIG. 12.
Figure 13B:
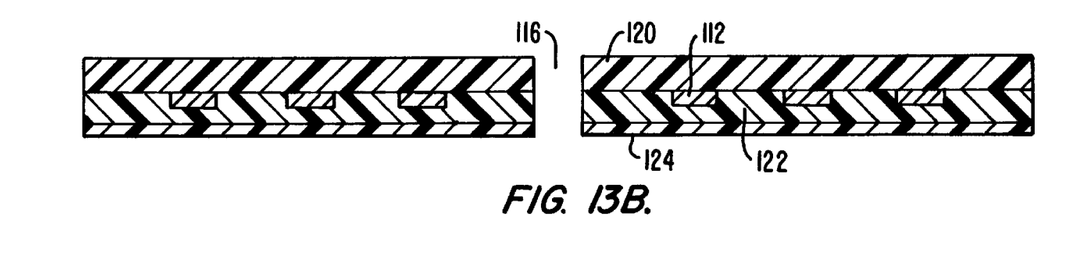
Figure 13C:
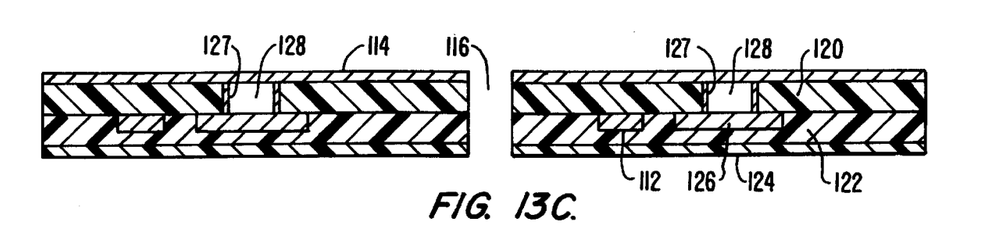
Figure 13D:
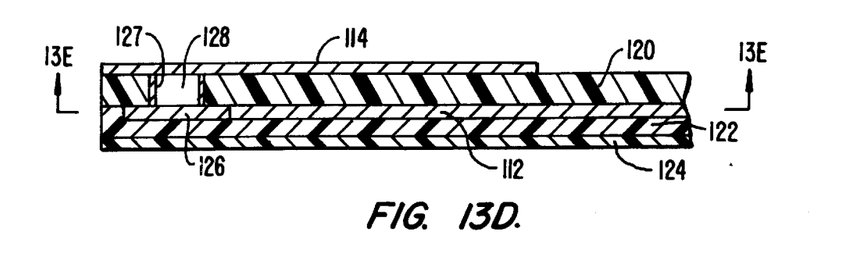
Figure 13E:
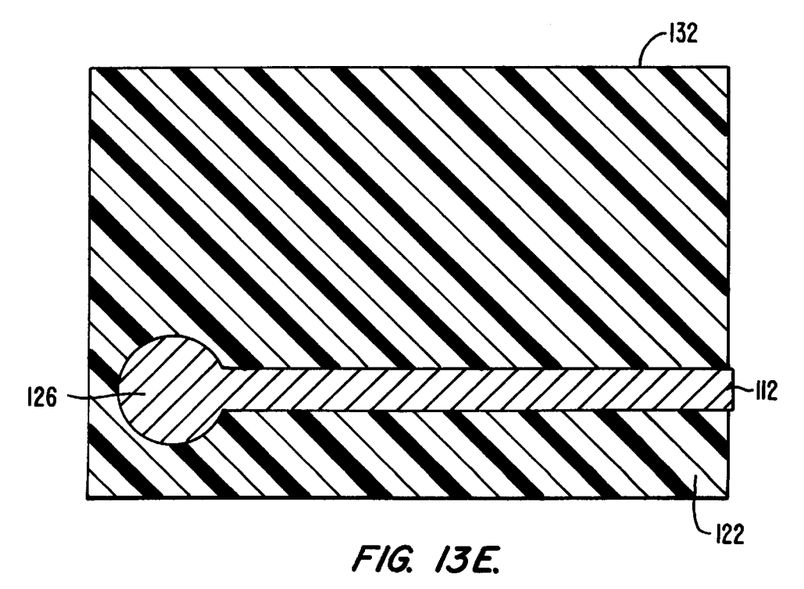
FIG. 13E is a cross-sectional view taken along line 13E—13E of FIG. 13D.

FIG. 13A illustrates the exposure of proximal terminals 108 through layers of material which constitutes flat flexible circuit 110. At FIG. 13B, flat flexible circuit 110 is seen to include a first polyimide layer 120, a polyimide adhesive layer 122 partially surrounding traces 112 and a second polyimide layer 124. FIG. 13C–13E are various cross-sectional views taken at electrode pads 114. The distal ends 126 of electrical traces 112 are enlarged and are electrically coupled to electrode pads 114 by "through-hole plating," a technique where a conductive copper layer 127 covers the walls of a hole 128 formed in first polyimide layer 120. A thin final plating of gold on electrode pads 114 enhances biocompatibility.

FIG. 14 illustrates an alternative embodiment of the structure shown in FIG. 13C. A polyimide sheet layer 120a has single-layer copper electrical traces 112a applied to one surface. Trace 112a is then covered by a polyimide adhesive layer 122a, layer 122a being covered by a second polyimide sheet layer 124a. Openings in the cover layer of polyimide sheet 124a and adhesive layer 122a expose the enlarged end portions of traces 112a which are selectively plated with copper and then a thin layer of gold to form electrode pads 114a. Pads 114a extend above second sheet layer 124a and serve as the electrodes. Other fabrication techniques are available to those skilled in the art of flexible circuit fabrication.

Figure 11A:
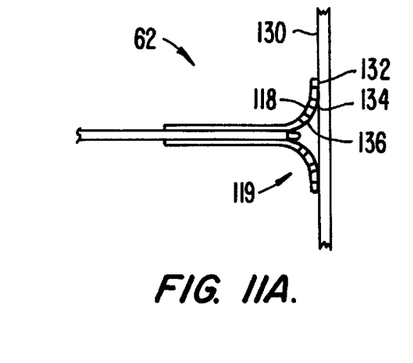
FIGS. 11A and 11B are simplified side views showing deployment of the electrode assembly of FIG. 8 shown with electrode arms engaging a flat surface in partially and fully engaged positions.
Figure 11B:
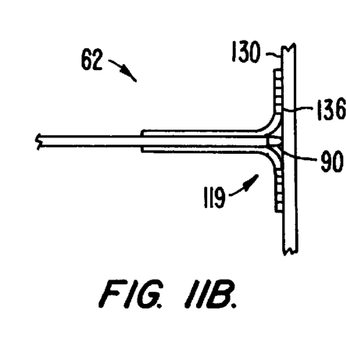

FIGS. 11A and 11B illustrate array 119 of electrode catheter 62 in simplified form with arms 118 pressed against a simulated heart chamber wall 130. While wall 130 is shown as flat, it could be, and typically is, curved in a variety of ways. Arms 118 are shown in FIG. 11A as only slightly flexed from their normal, deployed shape of FIG. 8. The outermost and intermediate electrode pads 132, 134 are, in the preferred embodiment, spaced apart by about 2.5 mm. This spacing could be changed, such as by being reduced to about 0.5 mm or enlarged to about 10 mm. In FIG. 11A pads 132, 134 engage chamber wall 130. Further force on electrode catheter 62, typically through core wire 78, causes arms 118 to further deflect so that innermost electrode pads 136 also contact surface 130 in FIG. 11B. In addition, tip electrode 90 is also in contact with chamber wall 130 in FIG. 11B.

Electrode pads 132, 134 are typically paired together while innermost electrode pads 136 are each paired with tip electrode 90 for mapping purposes. Tip electrode 90 can also be used for ablation when electrode catheter 62 is confirmed to be properly positioned at the target site. Much of the preliminary information as to the proper position of electrode catheter 62 can be obtained while the electrode catheter is in the partially engaged position of FIG. 11A. In some situations the necessary information for mapping and determining that electrode catheter 62 is properly positioned at the target site may require the electrode catheter to be fully engaged with chamber wall 30 as its shown in FIG. 11B. In either case sufficient information is quickly obtained to permit electrode catheter 62 to be moved, if necessary, to coincide with the target site.

In use, electrode catheter 62 is housed within delivery sheath 66 with outermost electrode pads 132 adjacent the distal end of sheath 66. Using lateral deflection knob 72 and tip deflection control 74, the distal end of electrode array catheter 60 is positioned within the heart chamber and near the target site. Electrode catheter 62 is then moved axially within delivery sheath 66 to the deployed position of FIGS. 8 and 9. This may occur by sheath 66 being retracted back over catheter 62 or by electrode catheter 62 being pushed out through sheath 66. Array 119 can be deflected laterally using manipulator wire 76 or torqued (rotated) using core wire 78. Arms 118 of array 119 are then directed against chamber wall 130 at what is hoped to be the target site so that mapping can occur. Once it has been determined that tip electrode 90 is properly over the target site to be ablated, electrode catheter 62 can be forced against chamber wall 130 such as shown in FIG. 11B and the target site ablated by supplying, typically, RF electrical energy to tip electrode 90 through power wire 104. In an alternate embodiment, the distal end of electrode array catheter 60 can be deflected laterally or torqued (rotated) by steering the tip of the delivery sheath, which would incorporate manipulator wire 76 and core wire 78 and a handle with appropriate controls.

Modification and variation can be made to the disclosed embodiments without departing from the subject of the invention as defined in the following claims. For example, reference has been made to pairs of electrodes for mapping purposes. Electrodes could, of course, be paired in other manners to provide different information. For example, instead of pairing innermost electrode pad 136 with tip electrode 90, the innermost electrode pad 136 on one arm 118 could be paired with the corresponding innermost electrode pad on an adjacent arm. Electrode assembly 2 could include a large electrode at the center of tip 24 aligned with body 6 to permit greater force to be exerted against such enlarged electrode when used for ablation. Flexible circuit 110 could be made by other techniques, such as lamination processes or direct wiring of electrode bands attached to radially disposed arms. Each arm 118 could be made as a separate flexible circuit instead of being formed by slitting a common circuit as shown in FIG. 12. The number of electrodes for use with the electrode assemblies could vary greatly, from only 4 to 1,000. Electrodes 26 could be paired differently from the closely-spaced bipoles illustrated, such as radially oriented bipoles. Electrode arms 118 could vary in number from 3 to at least 8. In both embodiments a delivery sheath is used to constrain the array of electrodes of the tip prior to deployment at the target site; if the tip can be kept constrained without the need for a delivery sheath, such sheath can be eliminated. Instead of super-elastic NiTi, core 14 could be made of heat-shape memory NiTi. This alloy, also available from Furukawa Electric Co. Ltd., can be used for core 14 so that tip 24 is flexible but straight below a transition temperature and is flexible and curved, such as illustrated in FIGS. 1 and 2A–2C, above the transition temperature. The transition temperature would be chosen so that after tip 24 is at or near the target site, core 14 could be heated (such as electrically or with a warm saline solution) so tip 24 assumes its predetermined curved shape. Similar heat-shape memory material could be used for electrode elements/arms 118 as well.

What is claimed is:

1. A steerable electrode array catheter, for insertion into a heart chamber for placement of multiple electrodes against the heart chamber wall in the vicinity of a target site, comprising:

an electrode assembly including a distal end, said distal end comprising:

a free, unattached tip;

an elongate electrode body which naturally assumes a curved shape when in an unconstrained, deployed position, said curved shape having one or more curved regions curving substantially more than 360°;

at least four electrodes mounted to the electrode body and positioned over more than about 360° of the one or more curved regions of the electrode body, said electrodes being electrically isolated from one another and naturally assuming an array when said distal end is unconstrained, said electrodes distributed along said distal end to be able to contact a portion of the chamber wall surrounding the target site, said portion being substantially less than the entire chamber wall;

means for steering the distal end of the electrode assembly within the heart chamber to the target site; and a flexible delivery sheath having a hollow interior, a proximal end and a distal end, the electrode assembly slidably mounted within the hollow interior of the delivery sheath for movement between a retracted position, at least substantially housed within the hollow interior, and a deployed position, extending from the distal end of the delivery sheath, the delivery sheath having an electrode at said distal end of the delivery sheath.

2. The catheter of claim 1 wherein the electrode assembly includes an ablation electrode.

3. The catheter of claim 2 wherein the ablation electrode includes a temperature sensing means for sensing the temperatures at a position adjacent the ablation electrode.

4. The catheter of claim 2 wherein the length of the ablation electrode is about 1 to 10 mm.

5. The catheter of claim 1 wherein at least some of said electrodes are arranged in pairs.

6. The catheter of claim 5 wherein the electrodes in said electrode pairs are spaced apart by about 0.5 mm–10 mm.

7. The catheter of claim 1 wherein said array is a three-dimensional array.

8. The catheter of claim 1 wherein said array is a two-dimensional array.

9. The catheter of claim 1 wherein the steering means includes means for directly deflecting the distal end of the electrode assembly.

10. The catheter of claim 9 wherein the directly deflecting means deflects the distal end of the electrode assembly laterally.

11. The catheter of claim 1 wherein the steering means includes means for deflecting the distal end of the delivery sheath.

12. The catheter of claim 11 wherein the deflecting means deflects the distal end of the delivery sheath laterally.

13. The catheter of claim 1 wherein the steering means includes means for rotating at least the distal end of the electrode assembly within the delivery sheath.

14. The catheter of claim 1 wherein the one or more curved regions curve about 720°.

15. The catheter of claim 1 wherein the electrode body is a resilient electrode body which includes a super-elastic NiTi spring material.

16. The catheter of claim 1 wherein at least substantially all of the electrodes are paired, said pairs being spaced apart along the electrode body.

17. The catheter of claim 1 wherein the electrode body naturally assumes a distally-extending, three-dimensional, coiled, conical shape when in the deployed position.

18. The catheter of claim 17 wherein the distally-extending, three-dimensional, coiled, conical shape is a diverging coiled conical shape.

19. The catheter of claim 1 wherein the electrode assembly includes at least one pair of ablation electrodes.

20. A method for performing an electrophysiology procedure at a target site within a heart chamber comprising the following steps:

selecting an electrode array catheter having a distal end, movable between constrained and unconstrained conditions, the distal end comprising a tip and an elongate electrode body, which naturally assumes a distally-extending, three-dimensional, coiled, conical shape when the distal end is in the unconstrained condition, said curved shape having one or more curved regions curving substantially more than 360°, the one or more curved regions of the electrode body comprising at least four electrodes electrically isolated from one another and arranged in distally-extending, three-dimensional, coiled, conical array when said distal end is in the unconstrained condition;

steering the distal end into the heart chamber;

unconstraining the distal end so that the electrode body assumes said curved shape with said curved regions curving substantially more than 360°, said electrodes extend over more than about 360° of the electrode body and said tip being free and unattached;

directing the array of electrodes against the endocardial wall within the heart chamber to the target site by remotely deflecting the distal end within the heart chamber; and performing a chosen electrophysiology procedure, said distally-extending, three-dimensional, coiled, conical curved shape of the distal end chosen so each said electrode engages the endocardial wall at the target site.

21. The procedure of claim 20 wherein the selecting step is carried out by selecting an electrode array catheter which has said array of electrodes sized to cover substantially less than the entire endocardial wall when said distal end is unconstrained.

22. The procedure of claim 20 further comprising the step of deploying, once the distal end is within the heart chamber, the distal end from the constrained condition to the unconstrained condition to permit said electrodes to assume said array.

23. The procedure of claim 20 wherein the remotely deflecting step is carried out by deflecting a distal end of a delivery sheath.

24. The procedure of claim 20 wherein the remotely deflecting step is carried out by directly deflecting the distal end of the electrode array catheter.

25. The procedure of claim 20 wherein the chosen procedure includes the step of mapping the endocardial wall at the target site.

26. The procedure of claim 20 wherein the chosen procedure includes the step of ablation of a portion of the endocardial wall at the target site.

27. The procedure of claim 26 wherein the ablation step is carried out using at least one pair of ablation electrodes.

28. An electrode array catheter, for insertion into a heart chamber for placement of multiple electrodes against the heart chamber wall in the vicinity of a target site, comprising:

an electrode assembly including a distal end, said distal end comprising:

an elongate electrode body which naturally assumes a distally-extending, three-dimensional, coiled, generally conical shape when in an unconstrained, deployed position; and at least four electrodes mounted to the electrode body and positioned over more than about 360° of electrode body, said electrodes being electrically isolated from one another and naturally assuming a distally-extending, three-dimensional, coiled, generally conical array when said distal end is unconstrained, said electrodes distributed along said distal end to be able to contact a portion of the chamber wall surrounding the target site, said portion being substantially less than the entire chamber wall.

29. The catheter according to claim 28 further comprising a flexible delivery sheath having a hollow interior, a proximal end and a distal end, the electrode assembly slidably mounted within the hollow interior of the delivery sheath for movement between a retracted position, at least substantially housed within the hollow interior, and a deployed position, extending from the distal end of the delivery sheath.

30. An electrode array catheter, for insertion into a heart chamber for placement of multiple electrodes against the heart chamber wall in the vicinity of a target site, comprising:

an electrode assembly including:

a distal end having a single elongate, resilient, conformable electrode body; and a plurality of electrodes distributed along the electrode body so that said electrodes naturally assume an array when said electrode body is unconstrained, said electrodes being distributed along the electrode body so as to be able to contact a limited portion of the chamber wall surrounding the target site;

a flexible delivery sheath, having a hollow interior, a proximal end and a distal end, the electrode assembly being slidably mounted within the hollow interior of the delivery sheath for movement between a retracted position, at least substantially housed within the hollow interior, and a deployed position, extending from the distal end of the delivery sheath; and the sheath having a distal tip which acts as an electrode.

31. The catheter of claim 30 wherein the electrode body naturally assumes a two-dimensional shape when unconstrained.

32. The catheter of claim 31 wherein the two-dimensional shape is a serpentine shape.

33. The catheter of claim 31 wherein the two-dimensional shape is a flat coil.

34. The catheter of claim 30 wherein the electrode body naturally assumes a three-dimensional, coiled, conical shape when in the deployed position.

35. The catheter of claim 34 wherein the coiled, conical shape is a diverging coiled, conical shape.

36. The catheter of claim 30 wherein the electrodes include a plurality of mapping/pacing electrodes and at least one ablation electrode.

37. The catheter of claim 30 wherein the electrode assembly includes a temperature-sensing ablation electrode.

* * * * *